United States Patent [19]

Teufel et al.

[11] 3,969,418
[45] July 13, 1976

[54] (4-BIPHENYLYL)-BUTENOLS

[75] Inventors: Helmut Teufel; Wolfhard Engel; Ernst Seeger, all of Biberach an der Riss, Germany

[73] Assignee: Boehringer Ingelheim GmbH, Ingelheim am Rhein, Germany

[22] Filed: July 3, 1974

[21] Appl. No.: 485,574

Related U.S. Application Data

[63] Continuation-in-part of Ser. No. 387,802, Aug. 13, 1973, Pat. No. 3,859,256.

[30] Foreign Application Priority Data

Aug. 17, 1972 Germany............................ 2240440

[52] U.S. Cl...................... 260/618 R; 260/618 D; 424/343
[51] Int. Cl.²................... C07C 31/14; C07C 31/34
[58] Field of Search..................... 260/618 D, 618 R

[56] References Cited
UNITED STATES PATENTS

| | | | |
|---|---|---|---|
| 2,055,437 | 9/1932 | Croll et al........................ | 260/618 R |
| 2,921,940 | 11/1960 | Ramsden......................... | 260/618 R |
| 3,700,738 | 10/1972 | Byrowth et al.................. | 260/618 R |

*Primary Examiner*—Raymond V. Rush
*Assistant Examiner*—D. B. Springer
*Attorney, Agent, or Firm*—Hammond & Littell

[57] ABSTRACT

Compounds of the formula

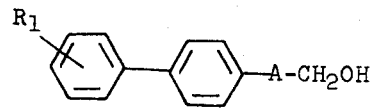

wherein A is

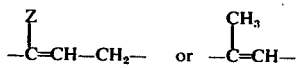

or
where Z is hydrogen or methyl, and $R_1$ is halogen or, when A is

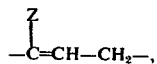

also hydrogen,
the compounds are useful as antiphlogistics.

4 Claims, No Drawings

(4-BIPHENYLYL)-BUTENOLS

This is a continuation-in-part of copending application Ser. No. 387,802, filed Aug. 13, 1973, now U.S. Pat. 3,859,256.

This invention relates to novel (4-biphenylyl)-butenols, as well as to various methods of preparing these compounds.

More particularly, the present invention relates to compounds of the formula

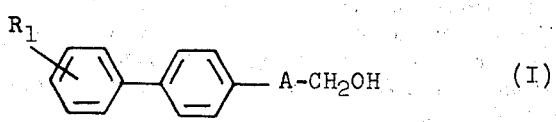   (I)

wherein A is

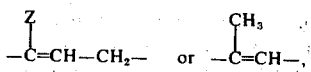

where Z is hydrogen or methyl, and R₁ is halogen or, when A is

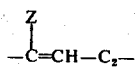

also hydrogen.

The compounds embraced by formula I above may be prepared by a number of different methods, among which the following have proved to be particularly convenient and efficient.

Method A

By reducing a compound of the formula

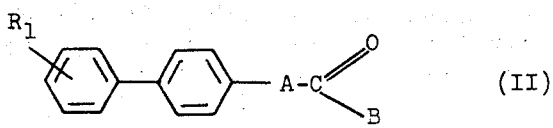   (II)

wherein A and R₁ have the same meanings as in formula I, and
B is hydroxy, alkoxy, aralkoxy, aryloxy, acyloxy or halogen,
with a complex hydride.

Suitable complex hydrides include, for example, the complex metal hydrides, such as lithium aluminum hydride, lithium borohydride or alkoxy aluminum hydrides, such as sodium-bis-(2-methoxyethoxy)-dihydroaluminate, or also sodium borohydride together with anhydrous aluminum chloride or with boron trifluoride. Compounds of the formula II, wherein A has the same meanings as defined above and B is halogen, may also be reduced with sodium borohydride only.

The reduction is carried out in a suitable inert organic solvent like tetrahydrofuran, ether, dimethoxyethane, diethylene glycol dimethyl ether, benzene or in mixtures thereof at temperatures between 0°C and the boiling point of the solvent used, preferably at temperatures between 0° and 30°C.

Some starting compounds of the formula II are disclosed in copending U.S. patent application Ser. No. 289,008, filed Sept. 14, 1972.

Method B

For the preparation of compounds of the formula I, wherein A is

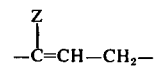

compounds of the formula

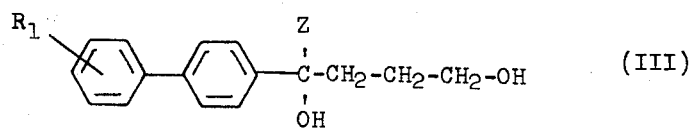   (III)

wherein Z and R₁ have the same meanings as in formula I, are dehydrated in the presence of a dehydrating agent. As a dehydrating agent, hydrogen halide salts of tertiary organic bases may especially be considered. The tertiary organic bases, for example, pyridine, alkylpyridine, N,N-dialkylaniline or N-alkylpiperidine have proved to be suitable; and as hydrogen halides, especially hydrogen chloride and hydrogen bromide, may be mentioned. Especially preferred as a dehydrating agent is pyridine hydrochloride. The reaction may be carried out without a solvent, in some cases, however, the presence of a solvent is preferred. The compounds of the formula III with the dehydrating agent, is heated up to temperatures between 100° to 200°C. Suitable solvents include toluene, xylene or dichlorobenzene.

Some starting compounds of the formula III are disclosed in copending U.S. patent application Ser. No. 295,880, filed Oct. 10, 1972.

Compounds of the formula II, used as starting material wherein A is

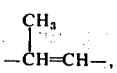

and
B is hydroxy, alkoxy, aralkoxy or aryloxy may be obtained by dehydration of compounds of the formula II, wherein A is

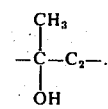

As dehydrating agents, acidically reacting salts like those of pyridine or alkylpyridine with hydrohalogen acids, furthermore potassium hydrogen sulfate or metal salts like zinc chloride or acids like p-toluenesulfonic acid, phosphoric acid, sulfuric acid or acid chlorides like phosphorus oxychloride, may be considered. The reaction is generally carried out in an inert solvent like toluene, benzene or xylene at temperatures up to the boiling temperature of the solvent used.

The starting compounds of the formula II, wherein A is

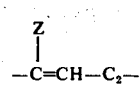

may be prepared from compounds of the formula

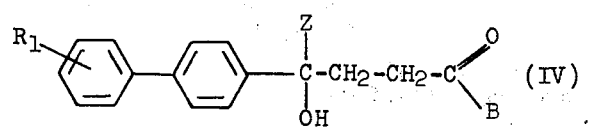

or from lactones of the formula

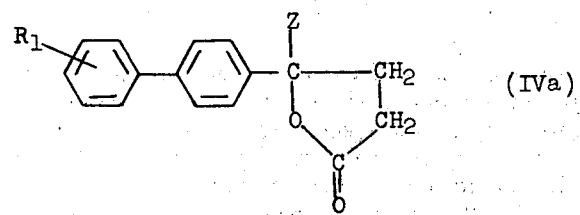

where $R_1$, Z and B have the same meanings as defined above, by dehydration in the presence of hydrogen halide salts of tertiary organic bases. The dehydration is carried out at temperatures between 140° and 200°C. As tertiary organic bases, for example, pyridine and alkyl pyridine and hydrohalogen acid, hydrochloric acid, may be used.

If A is

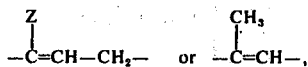

the acid halides may be prepared from the compounds of the formula II, wherein B is hydroxy, according to known methods, for example, by treatment with phosphorus halides or thionylchloride.

Compounds of the formula IV,
wherein Z is methyl, and
B is hydroxy,
may for example be obtained from the corresponding lactones of the formula IVa. These lactones are prepared by condensation of a succinic acid ester with a correspondingly substituted 4-biphenylyl-methyl-ketone in the presence of an alkali metal alcoholate and subsequent saponification and decarboxylation of the obtained semi-ester (see Johnson et al, Org. Reactions 6, 1 [1951]).

Compounds of the formula II, wherein A is

can also be obtained by condensation of an aldehyde of the formula

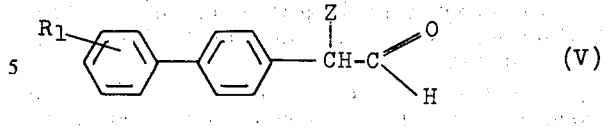

with malonic acid in the presence of pyridine or piperidine, first at room temperature, then at temperatures up to the boiling point of pyridine. The aldehydes of the formula V may for example be obtained by glycideester-condensation according to Darzens-Erlenmeyer-Claisen or, if Z is methyl, by isomerization of oxiranes of the formula

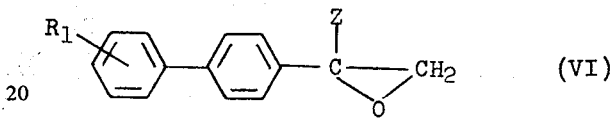

in the presence of boron trifluoride etherate. The oxiranes of the formula VI are for example obtained by reaction of dimethyl sulfonium methylide with corresponding 4-biphenylyl methyl ketones.

The starting compounds of the formula III, wherein Z is hydrogen, are for example obtained by reduction by means of complex hydrides of 4-(4-biphenylyl)-4-oxo-butyric acid esters. As a complex hydride, especially sodium borohydride in the presence of anhydrous aluminum chloride at room temperature and in the presence of a suitable solvent, such as dioxane, may be used.

The starting compounds of the formula III, wherein Z is methyl, may for example be obtained by reduction of a lactone of the formula IVa by means of complex metal hydrides, for example by means of lithium borohydride or lithium aluminum hydride. The reduction is carried out in a solvent, such as tetrahydrofuran or ether, at temperatures up to the boiling point of the solvent used.

The following examples further illustrate the present invention and will enable others skilled in the art to understand it more completely. It should be understood, however, that the invention is not limited solely to the particular examples given below.

EXAMPLE 1

4-(4'-biphenylyl)-3-buten-1-ol by method A

A solution of 6.0 gm (0.025 mol) of 4-(4'-biphenylyl-3-butenoic acid (m.p. 188°C) in 100 ml of absolute tetrahydrofuran was dropwise stirred, at room temperature, into a suspension of 1.0 gm (0.026 mol) of lithium aluminum hydride in 100 ml of absolute ether. The mixture was stirred for a further 2 hours, then were successively added 1 ml of water, 2 ml of 2N sodium hydroxide solution and again 5 ml of water and the obtained precipitate was suction filtered. The solvent was distilled off from the filtrate, and the obtained firm residue was recrystallized from cyclohexane/ethyl acetate. The compound was obtained therefrom in a yield of 3.8 gm (68% of theory), m.p. 142°C, of the formula

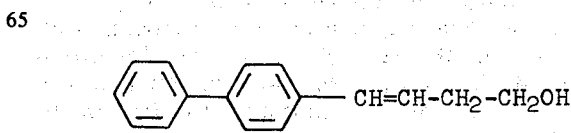

EXAMPLE 2

Using a procedure analogous to that described in Example 1, 4-(2''-fluoro-4'-biphenylyl)-3-buten-1-ol, m.p. 79°–80°C, was prepared from 4-(2''-fluoro-4'-biphenylyl)-3-butenoic acid, m.p. 142°–144°C, with a yield of 73% of theory, and having the formula

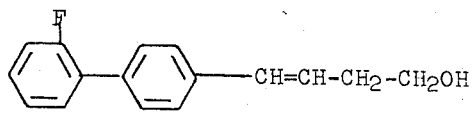

EXAMPLE 3

4-(2''-chloro-4'-biphenylyl)-3-buten-1-ol by method B 25.0 gm (0.09 mol) of 1-(2''-chloro-4'-biphenylyl) 1,4-butanediol were heated for 30 minutes while stirring with 80 gm of pyridine hydrochloride up to 150°C. Then water was added and the precipitated oil was absorbed in ether. The solvent was distilled off from the ethereal solution, which previously had been washed with water, dried and filtered over charcoal. The crude product (15 gm) was dissolved in ethylene chloride and subject to chromatography through silica gel. Ethylene chloride was used as eluents. The first fraction was thrown away. The second fraction consisted of the compound 4-(2''-chloro-4'-biphenylyl)-3-buten-1-ol, which melted clearly at 70°C, with a yield of 4 gm, and had the formula

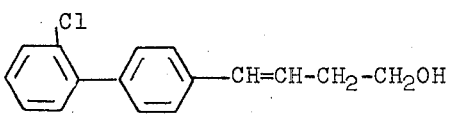

EXAMPLE 4

4-(2''-fluoro-4'-biphenylyl)-3-penten-1-ol by method A

A solution of 6.1 gm (0.021 mol) of crude ethyl 4-(2''-fluoro-4'-biphenylyl)-3-pentenate in about 500 ml of absolute ether was added dropwise within half an hour to a suspension of 1 gm (0.026 mol) of lithium aluminum hydride in 50 ml of absolute ether. After stirring for 2 hours at laboratory temperature the mixture was refluxed for 2 ½ hours. After cooling, first 1 ml of water, then 1 mol of 15% sodium hydroxide solution and then again 2 ml of water were carefully added for decomposition. The mixture was stirred for 1 to 1 ½ hours and filtered. From the filtrate 3.8 gm (83.7%) of 4-(2''-fluoro-4'-biphenylyl)-3-penten-1-ol, m.p. 102°–102.5°C, were obtained by evaporation and subsequent recrystallization from cyclohexane, and had the formula

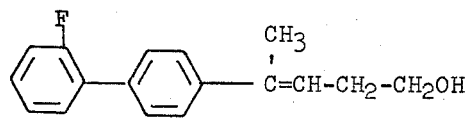

EXAMPLE 5

Using a procedure analogous to that described in Example 4, 4-(4'-biphenylyl)-3-penten-1-ol, m.p. 109°–110.5°C, was prepared from ethyl 4-(4'-biphenylyl)-3-pentenate, of the formula

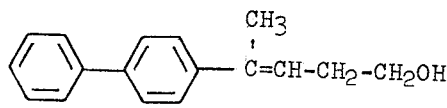

EXAMPLE 6

3-(2''-fluoro-4'-biphenylyl)-2-buten-1-ol by method A

A solution of 8.5 gm (0.03 mol) of ethyl 3-(2''-fluoro-4'-biphenylyl)-2-butenate, m.p. 52°–54°C, in 50 ml of absolute ether was added dropwise while stirring at room temperature into a suspension of 1.7 gm (0.045 mol) of lithium aluminum hydride in 150 ml of absolute ether. Afterwards stirring was continued for 90 minutes at room temperature, then successively 2 ml of water, 4 ml of 2N sodium hydroxide solution and again 10 ml of water were added and the precipitate was vacuum filtered and thrown away. The filtrate was washed with water, dried and the solvent was removed. The yield was 6.2 gm (85.2% of theory) of 3-(2''-fluoro-4'-biphenylyl)-2-buten-1-ol, m.p. 90°C, of the formula

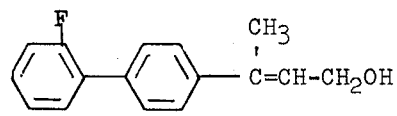

EXAMPLE 7

3-(2''-chloro-4'-biphenylyl)-2-buten-1-ol by method A

A solution of 15 gm (0.05 mol) of ethyl 3-(2''-chloro-4'-biphenylyl-2-butenate m.p. 77°–80°C, in 50 ml of absolute ether was added dropwise while stirring and cooling to 0° – 10°C into a suspension of 1.9 gm (0.05 mol) of lithium aluminum hydride in 200 ml of absolute ether. After finishing the addition the stirring was continued for 10 minutes while cooling, then successively 2 ml of water, 2 ml of 2N sodium hydroxide solution and again 6 ml of water were added. The obtained precipitate was vacuum filtered and thrown away. The solvent was evaporated from the filtrate. The remaining oil was purified by column chromatography through 200 gm of silica gel (0.2 to 0.5 mm) with the use of ethylene chloride as solvent. The residue remaining after evaporation of the ethylene chloride, was distilled yielding 5 gm (39% of theory) of 3-(2''-chloro-4'-biphenylyl)-2-buten-1-ol, b.p. 170°–172°C at 0.2 mm Hg, of the formula

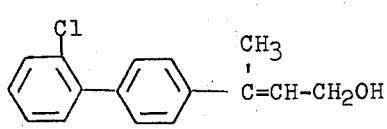

The compounds of the present invention, that is, those embraced by formula I above, have useful pharmacodynamic properties. More particularly, these compounds exhibit an antiphlogistic activity in warm-blooded animals, such as rats.

The above pharmacodynamic activity of the compounds of the present invention, namely their antiphlogistic activity and their toxicity, were ascertained in the manner described below. While all of these compounds were found to have effective antiphlogistic activity, some illustrative test results are shown in Table I, where A = 4-(2''-fluoro-4'-biphenylyl)-3-buten-1-ol, and
B = 4-(4'-biphenylyl-3-buten-1-ol.

The compounds were tested with respect to their antiexudative effect on the kaolin-induced edema and the carrageenin-induced edema of the hind paw of the rat and with respect to their acute toxicity after oral administration to rats, in comparison with phenylbutazone, a compound with known antiphlogistic activities.

a. Kaolin-induced edema of the hind paw of the rat

The kaolin edema was induced according to the method given by Hillebrecht [Arzneimittel-Forsch. 4, 607 (1954)] by subplantary injection of 0.05 ml of a 10% suspension of kaolin in a 0.85% sodium chloride solution. Measurement of the volume of the paws was effected using the technique of Doepfner and Cerletti [Int. Arch. Allergy Immunol. 12, 89 (1958)].

Male FW 49 rats having an average weight of 120 to 150 gm were fed with the test compounds 30 minutes before inducing the edema by means of an oesophageal tube. 5 hours after the provocation of the edema the averaged values of the swelling caused in the rats treated with the test compounds were compared with values measured on control animals. By graphical extrapolation, the dose leading to a 35% reduction of the swelling ($ED_{35}$) was calculated from the presentage reduction values measured by the administration of different doses.

b. Carrageenin-induced edema of the hind paw of the rat

The provocation of the carrageenin edema was effected according to the method of Winter et al [Proc. Soc. exp. Biol. Med. 111, 544 (1962)] by subplantary injection of 0.05 ml of a 1% solution of carrageenin in a 0.85% solution of sodium chloride. The test compounds were administered 60 minutes before the provocation of the edema.

For the calculation of the reductive effect on the edema the values measured 3 hours after the provocation of the edema were used. All the other details were the same as described above in the case of the kaolin-induced edema.

c. Acute toxicity

After oral administration to male and female FW 49 rats (ratio 1:1) having an average weight of 135 gm, the acute toxicity ($LD_{50}$) was determined. The substances were fed as a trituration in Tylose.

The calculation of the $LD_{50}$ values was effected, as far as possible according to the method of Litchfield and Wilcoxon, based on the percentage of animals which died within 14 days after administration of the different doses.

d. Therapeutic Index

The therapeutical index (a measure for the therapeutic usefulness) was calculated as the quotient of the oral $LD_{50}$ and of the $ED_{35}$ value calculated from the anti-exudative effect (average value from the kaolin-edema and the carrageenin-edema).

The results obtained from the tests were recorded in the following Table I.

The above mentioned compounds surpass the known compound phenylbutazone in their antiphlogistic activity.

As the toxicity did not rise in proportion to the antiphlogistic effect, the compounds embraced by formula I have a therapeutic index of at least twice that of phenylbutazone.

TABLE I

| Compound | Kaolin edema $ED_{35}$ per os mgm/kg | Carrageenin edema $ED_{35}$ per os mgm/kg | Average value $ED_{35}$ mgm/kg | Acute Toxicity in the rat mgm/kg | Confidence limits (95% probability) | Therapeutical Index Ratio between toxic and antiexudative activity $LD_{50}/ED_{35}$ |
|---|---|---|---|---|---|---|
| Phenyl-butazone | 58 | 69 | 63.5 | 864 | 793–942 | 13.6 |
| A | 44 | 19 | 31.5 | 1770 | 1341–2326 | 56.2 |
| B | 42 | 50 | 46 | >2000 | * | >43.5 |

* 0 out of 10 animals died after application of 2000 mgm/kg per os

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antiphlogistic dosage unit of the compounds according to the present invention is from 0.83 to 6.67 mgm/kg body weight, preferably 1.33 to 5.0 mgm/kg body weight. The daily dose rate is from 1.66 to 16.7 mgm/kg body weight, preferably 2.5 to 10 mgm/kg body weight.

The following examples illustrate a few pharmaceutical dosage unit compositions comprising a compound of the present invention as an active ingredient and represent the best mode contemplated of putting the invention into practical use. The parts are parts by weight unless otherwise specified.

EXAMPLE 8

Tablets

The tablet composition was compounded from the following ingredients:

| | |
|---|---|
| 4-(2''-fluoro-4''-biphenyl)-3-buten-1-ol | 200.0 parts |
| Corn starch | 97.0 parts |
| Polyvinyl pyrrolidone | 10.0 parts |
| Magnesium stearate | 3.0 parts |
| Total | 310.0 parts |

Preparation

The active ingredient was admixed with corn starch, granulated with a 14% solution of polyvinylpyrrolidone in water passed through a screen of 1.5 mm, dried at 45°C, and passed once more through the said screen. The granulate thus obtained was admixed with magnesium stearate and compressed into tablets weighing 310 mgm. Each tablet contained 200 mgm of the (4-biphenylyl)-butenol and was an oral dosage unit composition with effective antiphlogistic activity.

EXAMPLE 9

Coated Tablets

The tablet core composition was compounded from the following ingredients:

| | | |
|---|---|---|
| 4-(4'-biphenylyl)-3-buten-1-ol | 200.0 | parts |
| Corn starch | 70.0 | parts |
| Gelatin | 8.0 | parts |
| Talcum | 18.0 | parts |
| Magnesium stearate | 4.0 | parts |
| Total | 300.0 | parts |

Preparation

The mixture of active ingredient and corn starch was granulated with an aqueous 10% solution of the gelatin through a 1.5 mm-mesh screen, dried at 45°C, and again passed through the said screen. The granulate thus obtained was admixed with talcum and magnesium stearate and compressed into tablet cores, each weighing 300 mgm. The tablet cores were subsequently coated by known method with a thin shell consisting essentially of a mixture of sugar and talcum, and finally polished with beeswax. Each coated tablet contained 200 mgm of the butenol derivative and was an oral dosage unit composition with effective antiphlogistic activity.

EXAMPLE 10

Gelatin Capsules

The capsule filler composition was compounded from the following ingredients:

| | | |
|---|---|---|
| 4-(2''-fluoro-4'-biphenylyl)-3-penten-1-ol | 200.0 | parts |
| Corn starch | 190.0 | parts |
| Colloidal silicic acid | 6.0 | parts |
| Magnesium stearate | 4.0 | parts |
| Total | 400.0 | parts |

Preparation

The ingredients were intimately admixed with each other, and 400 mgm portions of the mixture were filled into No. 1 gelatin capsules. Each capsule contained 200 mgm of the (4-biphenylyl)-butenol and was an oral dosage unit composition with effective antiphlogistic activity.

EXAMPLE 11

Suppositories

The suppository composition was compounded from the following ingredients:

| | | |
|---|---|---|
| 4-(4'-biphenylyl)-3-penten-1-ol | 300.0 | parts |
| Suppository base (e.g. cocoa butter) | 1450.0 | parts |
| Total | 1750.0 | parts |

Preparation

The active ingredient was finely powdered and stirred into the molten suppository base at 40°C, using an immersion homogenizer. 1750 mgm-portions of the mixture at 38°C were poured into cooled suppository molds and allowed to cool therein. Each suppository contained 300 mgm of the (4-biphenylyl)-butenol and was a rectal dosage unit composition with effective antiphlogistic activity.

EXAMPLE 12

Suspension

The suspension was compounded from the following ingredients:

| | | |
|---|---|---|
| 3-(2''-chloro-4'-biphenylyl)-2-buten-1-ol | 4.0 | parts |
| Dioctyl sodium sulfosuccinate (DONSS) | 0.02 | parts |
| Benzoic acid | 0.1 | parts |
| Sodium cyclamate | 0.2 | parts |
| Colloidal silicic acid | 1.0 | parts |
| Polyvinyl pyrrolidone | 0.1 | parts |
| Glycerol | 1.0 | parts |
| Flavoring | 0.1 | parts |
| Distilled water q.s.ad | 100.0 | parts by vol. |

Preparation

The DONSS, benzoic acid, sodium cyclamate and polyvinylpyrrolidone were successively dissolved in distilled water which had been heated to 70°C. The glycerol and colloidal silicic acid were then added, and the mixture was cooled to room temperature. The finely powdered active ingredient was then suspended in the mixture by means of an immersion homogenizer. The flavoring was added to the suspension which was then diluted with distilled water to the indicated volume. Each 5 ml of the suspension contained 200 mgm of the (4-biphenylyl)-butenol and was an oral dosage unit composition with effective antiphlogistic activity.

Analogous results are obtained when any one of the other compounds embraced by formula I is substituted for the particular (4-biphenylyl)-butenol in Examples 8 through 12. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

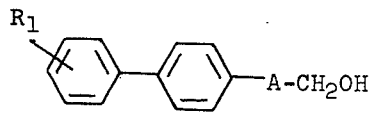

wherein A is

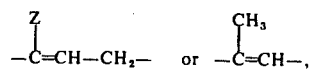

where Z is hydrogen or methyl, and
$R_1$ is halogen or, when A is

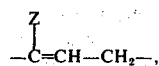
also hydrogen.
2. The compound according to claim 1, which is 4-(2''-fluoro-4'-biphenylyl)-3-buten-1-ol.
3. The compound according to claim 1, which is 4-(4'-biphenylyl-3-buten-1-ol.
4. The compound according to claim 1, which is 3-(2''-chloro-4'-biphenylyl)-2-buten-1-ol.
* * * * *

PO-1050
(5/69)

UNITED STATES PATENT OFFICE
CERTIFICATE OF CORRECTION

Patent No. 3,969,418    Dated July 13, 1976

Inventor(s) HELMUT TEUFEL, WOLFHARD ENGEL and ERNST SEEGER

It is certified that error appears in the above-identified patent and that said Letters Patent are hereby corrected as shown below:

Col. 1, line 35    That portion of the formula which reads "$-C_2-$" should read -- $-CH_2-$ --

Col. 3, line 6    That portion of the formula which reads "$-C_2-$" should read -- $-CH_2-$ --

Signed and Sealed this

Second Day of November 1976

[SEAL]

*Attest:*

RUTH C. MASON
*Attesting Officer*

C. MARSHALL DANN
*Commissioner of Patents and Trademarks*